US00PP31194P2

(12) United States Plant Patent
Chen et al.

(10) Patent No.: US PP31,194 P2
(45) Date of Patent: Dec. 10, 2019

(54) PEACH TREE NAMED 'CRIMSON JOY'

(50) Latin Name: ***Prunus persica* (L.) Batsch**
Varietal Denomination: Crimson Joy

(71) Applicant: The United States of America, as Represented by the Secretary of Agriculture, Washington, DC (US)

(72) Inventors: Chunxian Chen, Byron, GA (US); William R. Okie, Warner Robins, GA (US)

(73) Assignee: The United States of America, as Represented by the Secretary of Agriculture, Washintgon, DC (US)

( * ) Notice: Subject to any disclaimer, the term of this patent is extended or adjusted under 35 U.S.C. 154(b) by 0 days.

(21) Appl. No.: 16/350,684

(22) Filed: Dec. 19, 2018

(51) Int. Cl.
*A01H 5/08* (2018.01)
*A01H 6/74* (2018.01)

(52) U.S. Cl.
USPC ..... Plt./198

(58) Field of Classification Search
USPC ..... Plt./198
CPC ..... A01H 5/08; A01H 6/74
See application file for complete search history.

*Primary Examiner* — Annette H Para
(74) *Attorney, Agent, or Firm* — John D. Fado; Ariel L. Atkinson

(57) ABSTRACT

A new and distinct variety of peach tree, denominated 'Crimson Joy', has firm, freestone, melting, yellow flesh fruit with normal acidity, and good eating quality. The fruit typically ripen approximately with 'Harvester' and about one week after 'GaLa' in early to mid-June in Byron, Ga., have a high percentage of red blush with an attractive yellow ground color on skin surface, and usually are almost round. The tree is moderately vigorous and semi-spreading in growth habit, has self-fertile showy pink flowers, and regularly bears heavy annual crops. This variety has a winter chilling requirement estimated at approximately 700 chill hours and is suited for medium to high chill areas.

4 Drawing Sheets

Latin name of the genus and species of the plant claimed: 'Crimson Joy' is a peach tree that is a *Prunus persica* (L.) Batsch.

Variety denomination: The new peach tree is of the variety denominated 'Crimson Joy'.

BACKGROUND OF THE NEW PLANT

The present invention relates to a new and distinct variety of fresh-market peach designated 'Crimson Joy' and botanically known as *Prunus persica* (L.) Batsch. This new peach tree is adapted to a Southeastern subtropical climate with medium high chill in winters. 'Crimson Joy' variety resulted from open-pollination of BY96P3423 (an advanced selection, unpatented) yellow peach, which resulted from a hand-pollinated cross between 'Blazeprince' (the seed parent, unpatented) and BY91P2435 (an advanced selection, the pollen parent, unpatented) yellow peaches. 'Crimson Joy' variety was obtained by hybridizing and propagated by grafting on 'Guardian'® rootstock trees. It has desired chilling requirement (~700 hours, alternative to other main-season cultivars) and cropped relatively well in years with inadequate chill and spring freezes, making it less vulnerable to the adverse weather conditions in Byron, Ga. and worthy for trial for commercial fresh fruit production. Clonal plants were asexually propagated from the original 'Crimson Joy' tree by grafting in Byron, Ga. These asexually propagated plants, along with all characteristics of the tree and the fruit, remained true-to-type to the original 'Crimson Joy' tree. There are no known effects of the standard rootstock on the scion cultivar characteristics.

'Crimson Joy', produces firm, semi-freestone, melting, yellow-flesh fruit with normal acidity, good eating quality, and attractive blush, ripening in early to mid-June in Byron, Ga. 'Crimson Joy' is a promising candidate for commercial success in that it appears less vulnerable to inadequate chill and spring freezes in Byron, Ga., based on data in years with the conditions.

Byron, Ga. is under a subtropical climate. Winters are short, mild and with little snow; summers are long, hot and humid. The average January low temperature is about 1.2° Celsius and the average July high temperature is about 33.2° Celsius. The hours with temperatures below 7° Celsius vary often between 600 and 1200 hours per year. There are about 67 rainy days per year. Average annual precipitation (rainfall) is 1182.88 millimeter (46.57 inch) with great monthly and yearly variabilities and frequent thunderstorms in summers.

SUMMARY OF THE INVENTION

The new and distinct variety 'Crimson Joy' peach tree blooms late February to early March, approximately slight before or with 'Sunland' (unpatented) and slightly before 'GaLa' (unpatented) peach trees in Byron, Ga. The estimated chilling requirement, based on bloom time, is approximately 700 chill hours. The blooming period and the blooming date are dependent on climatic conditions. The flower anthers are yellow, and leaf glands are reniform, common characteristics of many standard peach varieties.

The first fruit of 'Crimson Joy' ripen generally in early to mid-June in Byron, Ga., approximately in the season of 'Harvester' (unpatented) and 'Redhaven' (unpatented) and one week after 'GaLa' (unpatented). 'Crimson Joy' trees are vigorous and productive, size well if not overcropped, and crop reliably. 'Crimson Joy' fruit have melting texture, good eating quality, and more blush coverage (approximately 90-100% red skin) than 'Harvester' (unpatented), 'Redhaven' (unpatented), and 'GaLa' (unpatented). There is some red pigmentation in the yellow flesh at the pit if allowed to mature on the tree. The potential for commercial production of fresh 'Crimson Joy' fruit is high, due to its attractive blush, reliable cropping characteristic, slightly lower chilling requirement, and less vulnerability to inadequate chill and spring freeze in Byron, Ga., compared to several other commercial cultivars ripening the same harvest window.

BRIEF DESCRIPTION OF THE PHOTOGRAPHS

The accompanying drawings are color photographs that are as nearly true as it is reasonably possible to make in a color illustration of this type:

FIG. 1 is a color photograph that shows a close view of typical fruits of the new variety 'Crimson Joy' at ripening time at Byron, Ga.

FIG. 2 is a color photograph that shows an attractive shape, exterior coloration, flesh, and pit of five specimens of 'Crimson Joy' fruit in a back side view (top left), a suture side view (top middle), a stem end view (bottom left), a blossom end view (bottom middle), and a fruit longitudinally cut into halves with and without the pit (top right and bottom right). Fruit are picked from an orchard at Byron, Ga.

Figure 1:
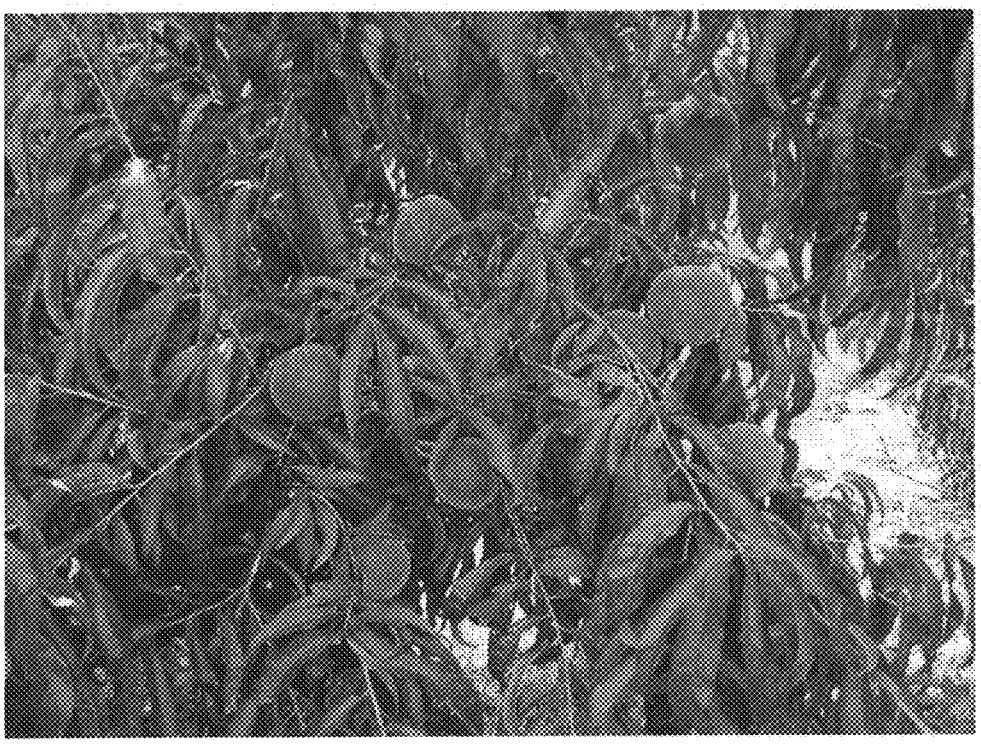
Figure 2:
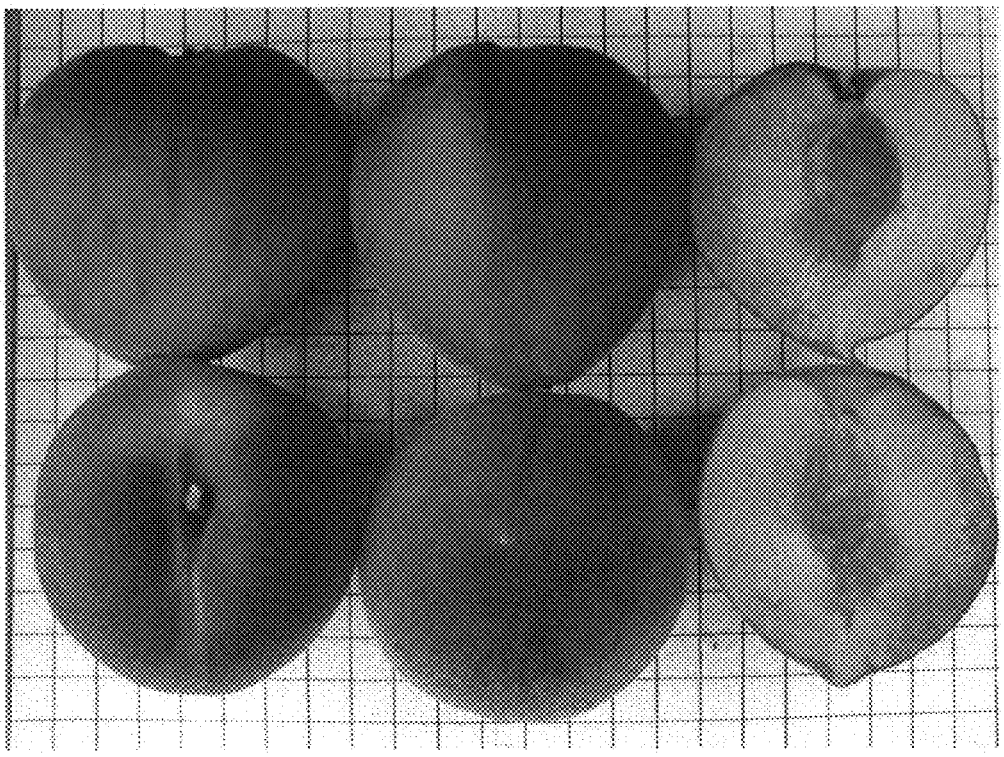
Figure 3:
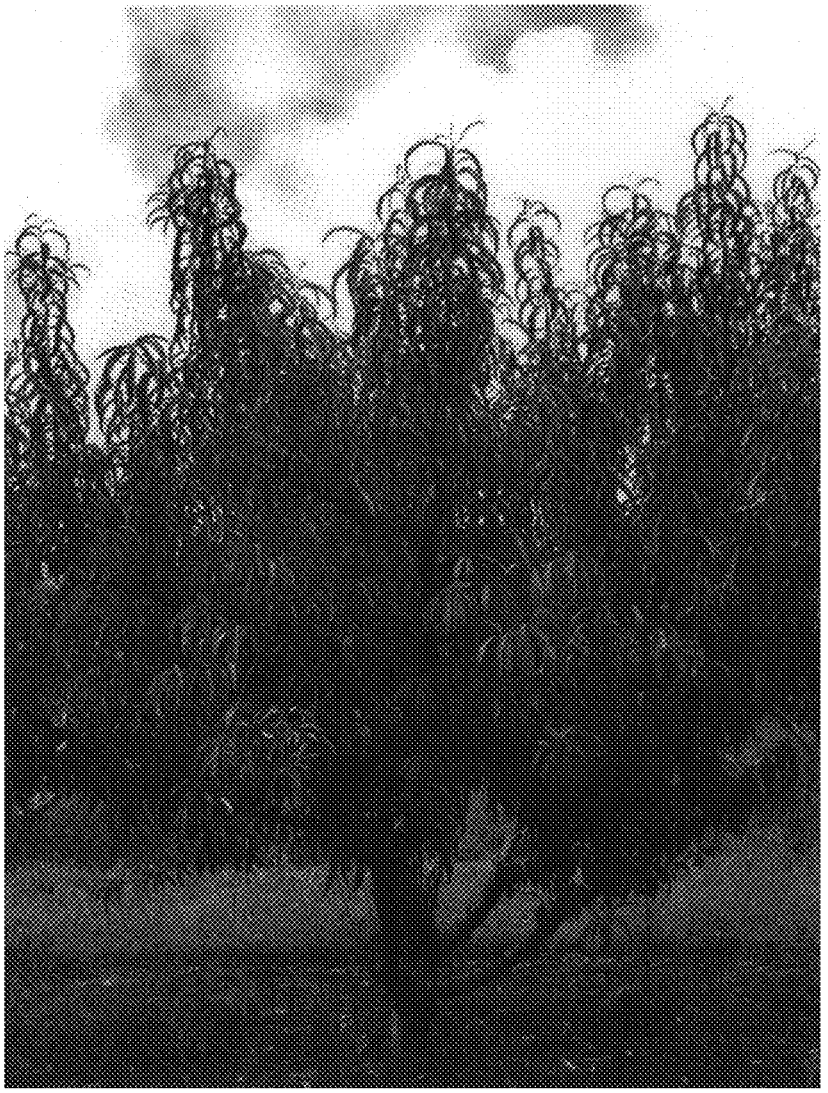
FIG. 3 is a color photograph that shows the typical semi-spreading architecture of an 8-year-old tree of the new variety 'Crimson Joy' at Byron, Ga.
Figure 4:
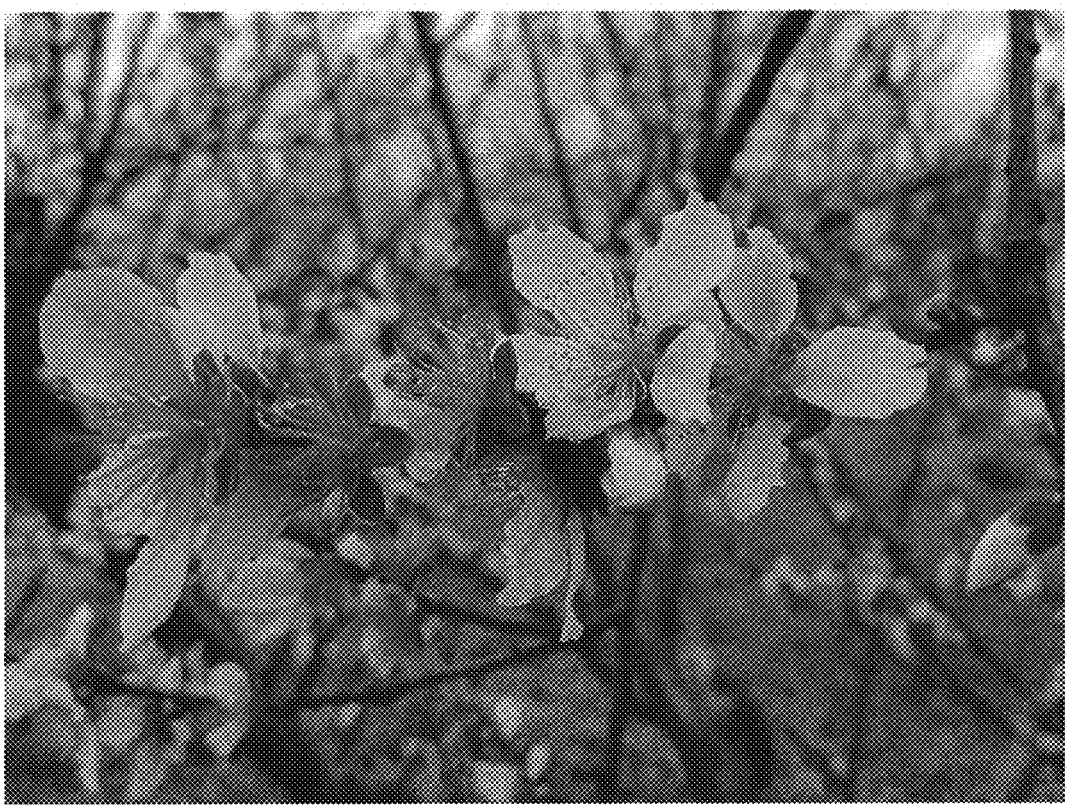
FIG. 4 is a color photograph that shows typical showy flowers of the new variety at Byron, Ga.

Due to photographical light, chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil types, cultural practices, climatic conditions, growing seasons, and development stages. Referring more specifically to the detailed botanical description of this new and distinct variety of yellow peach tree, the following was observed on 8-year-old trees of the variety grafted on 'Guardian'® rootstock under the ecological conditions prevailing at the orchards located at the town of Byron, Ga., USA. All major color code designations are by reference to the Royal Horticultural Society (R.H.S.) Colour Chart (Fourth Edition).

Tree:

*Size*.—Generally considered large when trained to an open vase form. The average height and width of 8-year-old tree are 2.80 meters and 4.60 meters, respectively, including current season shoots.

*Spread*.—Grown to a vase shape with summer and winter pruning to keep the tree open to get strong fruiting wood in the lower center.

*Vigor*.—Considered moderately vigorous. Trees respond typically to irrigation and fertilization in the orchards at Byron, Ga.

*Productivity*.—Very productive and regular, every year. Fruit set is spaced by thinning to develop the remaining fruit into desired market size. The fruit number varies with the prevailing climatic conditions and cultural practices.

*Bearer*.—Very regular without alternate bearing observed. The fruit is distributed homogenously on both short and long shoots and must be thinned to avoid limb breakage and obtain large fruit size.

*Form*.—Semi-spreading, but easily pruned to vase shape.

*Density*.—Considered dense. Pruning is required to open the tree center to promote sunlight entrance for enhancing fruit color and sugar.

*Hardiness*.—Hardy with respect to typical Georgia winters.

*Chilling requirement*.—Estimated endodormancy chilling requirement is approximately 700 chill hours based on time of bloom and leafing in relation to standard varieties.

Trunk:

*Size*.—Approximately 18.0 cm in diameter and at a height of approximately 280.0 centimeters on the 8-year-old trees at Byron, Ga.

*Bark texture*.—Generally smooth, but changes to light shaggy as tree ages.

*Bark color*.—RHS Greyed-Green Group 197A. Bark crack's color is RHS Brown Group 200C.

*Lenticels*.—Moderately low number, approximately 1 to 3 per square cm of surface area of trunk; and the average lenticel length and width of lenticels are approximately 6.78 millimeters and 2.43 millimeters, respectively.

*Lenticel color*.—RHS Greyed-Orange Group 197D.

Branches:

*Size*.—Average as compared to other peach varieties. Strong growth of scaffold branches. The current season mature fruiting branches have a diameter from 6.0 to 8.4 millimeters, and the average diameter is 7.09 millimeters. Tree growth and structure permits easier and faster winter pruning.

*Surface texture*.—Relatively smooth, numerous lenticels but smaller size than found on trunk and old scaffolds. Roughness increases with age.

*Crotch angles*.—Moderate to wide angles within the normal range of standard varieties for a semi-spreading tree after proper summer and winter pruning.

*Internode length*.—Approximately 1.7 to 2.9 centimeters with the average of 2.31 centimeters.

*Color of current season shoots*.—RHS Greyed-Orange Group 176C at the upper part (sunny side) of the shoots and RHS Yellow-Green Group 145B at the lower part (shady side) of the shoots.

*Color of mature branches*.—RHS Greyed-Orange Group 177A at the upper part (sunny side) of the shoots and RHS Greyed-Orange Group 177B at the lower part (shady side) of the shoots.

Leaves:

*Size*.—Considered medium to large for the species.

*Length*.—Approximately 15.4 to 18.9 centimeters with the average of 16.77 centimeters, not including the petiole.

*Width*.—Approximately 2.7 to 3.3 centimeters with the average of 3.07 centimeters.

*Thickness*.—Regular and average for commercial varieties, approximately 0.16 to 0.19 millimeters with the average of 0.18 millimeter, not noticeably unusual.

*Form*.—Lanceolate.

*Apex*.—Acute.

*Margin*.—Serrulate.

*Base*.—Acute.

*Surface*.—Upper, glabrous; Lower, medium large veins that are pinnately netted.

*Color*.—Regular green, slightly different in seasons. In early shoot growth, both upper and lower leaf surfaces are RHS Yellow-Green 151A. In late season, upper leaf surface is RHS Green Group 137B and lower surface is RHS Yellow-Green Group 147B. Leaf vein is RHS Yellow-Green Group 150D.

*Glands*.—Reniform. Usually 0-2 on lower leaf blade and 0-2 on petioles. Color is RHS Yellow-Green Group 146B.

*Petiole*.—Approximately 9.2 to 12.8 millimeters length with the average of 10.23 millimeters, approximately 1.6 to 2.0 millimeters diameter with the average of 1.77 millimeters. Color is RHS Yellow-Green Group 146B.

*Stipules*.—Medium, equal to most commercial peach varieties, visible on early young leaves, usually about 2 per leaf, and abscising just before leaves become full size in summer growth. Color at full size is RHS Yellow-Green Group 151A before abscising.

*Leaf blade incisions*.—Serrulate.

*Arrangement*.—Alternate.

Flowers:

*Flower buds*.—The form of flowers buds changes as blooming approaches, with variable dimensions. They are conic at pre-floral stage and approximately 6.5 to 7.3 millimeters long with the average of 6.81 millimeters and 3.5 to 4.3 millimeters wide with the average of 4.00 millimeters. The bud color in midwinter is RHS Greyed-Green Group 198A. The abundance is very high due to shorter than average internode length. Most buds set fruit in absence of spring frosts and show little evidence of bud drop.

*Hardiness*.—Hardy with respect to Georgia winters.

*Date of bloom*.—Late February to early March depending on winter chill hours and amount of warm weather.

*Blooming time*.—Considered early in bloom relative to other commercial peaches in central Georgia. Typically blooms slightly before or with 'Sunland' and slightly before 'GaLa'.

*Duration of bloom*.—Approximately 6 to 14 days. This characteristic varies significantly with chill hours accumulated in winter as well as temperatures during bloom.

*Bloom quantity*.—Generally abundant, with a good distribution.

*Flower bud frequency*.—Generally two flower buds per node, but occasionally one.

*Fragrance*.—Undetectable.

*Type*.—Showy.

*Size*.—Approximately 36.0 to 51.0 millimeters in diameter at full bloom, with the average of 44.30 millimeters.

*Petal*.—Size: Generally considered large. Length: approximately 21.2 to 23.6 millimeters with the average of 22.52 millimeters. Width: approximately 13.3 to 17.1 millimeters with the average of 15.51 millimeters. Form: generally round-shaped. Count: almost always five. Arrangement: usually free, sometimes touching. Texture: smooth, soft and glabrous. Color: RHS Red-Purple Group 62C in both the upper and lower surface. Margins: generally slightly undulating. Apex: generally round and curved-shaped.

*Pedicel*.—Length: approximately 4.1 to 8.3 millimeters with the average of 5.46 millimeters. Diameter: approximately 1.5 to 1.9 millimeters with the average of 1.71 millimeters.

*Calyx cup*.—Diameter: approximately 15.3 to 17.6 millimeters with the average of 16.47 millimeters. Color: RHS Green Group 139D at the interior surface and Red-Purple Group 59B at the exterior surface.

*Sepals*.—Number: generally five sepals. Length: approximately 6.3 to 7.4 millimeters with the average of 6.94 millimeters. Width: approximately 4.8 to 6.0 millimeters with the average of 5.53 millimeters. Color: RHS Red-Purple Group 59B.

*Stamen number*.—Approximately 31 to 45 stamens per flower with the average of 37.40.

*Anthers*.—Color: RHS Red Group 53B at opening.

*Pollens*.—Generally abundant and approximately RHS Yellow Group 15C.

*Filaments*.—Length at opening: approximately 10.0 to 12.4 millimeters with the average of 11.24 millimeters. The length of filaments is generally higher than that of pistils. Color: RHS Yellow-Green Group 150D.

*Pistil*.—Number: Usually one. Length: approximately 8.2 to 12.2 millimeters with the average of 10.20 millimeters and generally equal to stamen length, if not slightly smaller. Color: RHS Yellow-Green Group 150C.

Fruit:

*Maturity when described*.—Firm ripe for commercial picking.

*Date of harvest*.—Vary slightly with the prevailing climatic conditions. Harvest in 2018 at Byron, Ga. was June 13 until June 20.

*Size*.—Generally uniform, medium to large size. Weight: approximately 145.7 to 182.8 grams with the average of 163.67 grams. Equatorial diameter: approximately 60.3 to 72.4 millimeters with the average of 66.63 millimeters. Polar diameter (from stem to distal end): approximately 64.3 to 76.5 millimeters with the average of 70.91 millimeters. This characteristic highly depends on fruit number per tree, soil type, climatic conditions, and cultural practices, and therefore is not particularly distinctive of the variety.

*Peduncle*.—Length: approximately 4.0 to 5.3 millimeters with the average of 4.62 millimeters. Width: approximately 2.3 to 3.7 millimeters with the average of 2.91 millimeters. Color: RHS Green Group 138D.

*Longitudinal section form*.—Round, slightly squat.

*Transverse section through diameter*.—Generally round.

*Suture*.—Slightly ridged on suture.

*Ventral surface*.—Generally smooth, round.

*Shape of fruit base*.—Round to slightly cordate.

*Apex*.—Round to obtuse.

*Crater at stem attachment*.—Flaring oval to the suture. Depth: approximately 11.0 to 15.0 millimeters with the average of 13.30 millimeters. Width at top (cheek to cheek): approximately 21.0 to 32.0 millimeters with the average of 26.3 millimeters. Width at top (suture to back): approximately 29.0 to 40.0 millimeters with the average of 32.9 millimeters. Width at bottom (pedicel attachment): approximately 5.4 to 6.6 millimeters with the average of 5.89 millimeters.

*Skin*.—Thickness: generally medium in comparison to commercial peach varieties. Texture: generally typical of commercial peach varieties. Tenacity: Tenacious. Color: RHS Grey-Purple 187A, approximately 85% to 95% of skin. Fruit exposed to sunlight likely have a higher degree of enhanced skin color. Ground color: RHS Yellow 2C. Tendency to crack: None observed. Taste: No astringency observed. Epidermis: Typical short pubescence.

*Flesh*.—Ripens: evenly within each fruit. Texture: smooth, firm, melting, and juicy when fully ripe. Fibers: very fine, small, tender, and abundant. Aroma: moderate and typical of commercial peach varieties. Eating quality: excellent flavor with typical acidity for fresh market. Soluble solids content: approximately 10.2 to 11.9° Brix with the average of 11.35° Brix when at approximately 1.9 to 8.4 kgf of penetrometer firmness (the average is 5.07 kgf) with a standard 5/16-inch tip following a seven-day post-harvest storage protocol. This characteristic varies slightly with fruit number per tree, climatic conditions, cultural practices, and ripening stages. Color: RHS Yellow-Orange Group 17D. Color of red flecks within flesh: RHS Red Group 42B. Color of flesh at pit: RHS Yellow-Orange Group 17D. Browning by oxidation: none observed on tree ripe fruit beginning to soften. Amygdalin: none detected.

Stone:

*Type*.—Semi-freestone to freestone.

*Size*.—Generally medium large. The stone size varies upon the tree vigor, crop load and prevailing growing conditions. Length: approximately 29.2 to 35.9 millimeters with the average of 31.39 millimeters. Width: approximately 16.0 to 24.2 millimeters with the average of 21.78 millimeters. Diameter: approximately 16.1 to 17.8 millimeters with the average of 17.17 millimeters.

*Wall thickness*.—Approximately 4.5 to 6.9 millimeters with the average of 5.55 millimeters.

*Color*.—RHS Greyed-Orange 172B when flesh is freshly cut.

*Form*.—Oblong.

*Base*.—Straight.

*Apex*.—Acute.

*Sides*.—Generally equal.

*Surface*.—Generally furrowed toward ventral edge, smooth on dorsal edge and lighted pitted from base to apex.

*Tendency to split*.—None observed.

*Kernel*.—Viable if stratified upon removal from fruit at harvest, and without drying. Taste: bitter. Size: Considered medium large. Length: approximately 14.8 to 17.7 millimeters with the average of 16.7 millimeters. Width: approximately 8.2 to 10.7 millimeters with the average of 9.45 millimeters. Thickness: approximately 5.2 to 8.4 millimeters with the average of 5.87 millimeters. Form: generally acute apex with acute, sometimes straight base. Color: RHS Yellow-White 158B.

Use of the fruit: Fresh, dessert.

Keeping quality: Excellent after about two weeks at approximately 2 to 8 degrees Celsius and with little bruising or scarring appearing on skin.

Shipping quality: Considered very good. The fruit showed little bruising of the flesh or skin damage after normal harvesting and packing procedures. The fruit retained firmness and showed no internal breakdown of flesh or appreciable loss of eating quality under refrigeration at approximately 2 to 8 degrees Celsius indicates fruit should be highly acceptable for shipping.

Resistance to disease: Moderate to high resistance to bacterial spot incited by *Xanthomonas campestris* pv. *pruni*. No unusual resistance or susceptibility to insects and diseases was noted.

We claim:

1. A new and distinct variety of peach tree as illustrated and described, characterized by a medium high chilling requirement and bearing fruit having, yellow-fleshed fruit with normal acidity and melting, freestone with excellent eating quality a high percentage of red blush with an attractive yellow ground color, with fruit ripening in early to mid-June in Byron, Ga.

* * * * *